(12) United States Patent
John et al.

(10) Patent No.: US 8,354,243 B2
(45) Date of Patent: Jan. 15, 2013

(54) METHOD FOR DETERMINING PRESENCE OF CANCER IN A SAMPLE BY ASSAYING FOR EXPRESSION OF ECSA/DPPA-2 NUCLEOTIDE SEQUENCES

(75) Inventors: Thomas John, Heidelberg (AU);
Suzanne Svobodova, Heidelberg (AU);
Jonathan Cebon, Heidelberg (AU);
Otavia L. Caballero, New York, NY (US); Marilyn Monk, London (GB)

(73) Assignees: UCL Business plc, London (GB);
Ludwig Institute for Cancer Research, New York, NY (US)

( * ) Notice: Subject to any disclaimer, the term of this patent is extended or adjusted under 35 U.S.C. 154(b) by 307 days.

(21) Appl. No.: 12/310,802

(22) PCT Filed: Oct. 2, 2007

(86) PCT No.: PCT/US2007/021189
§ 371 (c)(1),
(2), (4) Date: Mar. 19, 2010

(87) PCT Pub. No.: WO2008/060370
PCT Pub. Date: May 22, 2008

(65) Prior Publication Data
US 2010/0210522 A1     Aug. 19, 2010

Related U.S. Application Data

(60) Provisional application No. 60/849,295, filed on Oct. 3, 2006.

(51) Int. Cl.
*G01N 33/574* (2006.01)
(52) U.S. Cl. ...................................... 435/7.23; 435/6.14
(58) Field of Classification Search .................. None
See application file for complete search history.

(56) References Cited

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*

* cited by examiner

*Primary Examiner* — Sheela J Huff
(74) *Attorney, Agent, or Firm* — Abelman, Frayne & Schwab

(57) ABSTRACT

The invention relates to the discovery of known molecule "DPPA-2" and a so-called "cancer-testis antigen." DPPA-2 is also a possible cancer stem cell marker. One can determine presence of cancer by assaying for the molecule, and also prevent or treat cancer via administration of the molecule.

5 Claims, No Drawings

METHOD FOR DETERMINING PRESENCE OF CANCER IN A SAMPLE BY ASSAYING FOR EXPRESSION OF ECSA/DPPA-2 NUCLEOTIDE SEQUENCES

RELATED APPLICATIONS

This application is a §371 from PCT/US2007/021189 filed Oct. 2, 2007, which claims priority from U.S. Application Ser. No. 60/849,295, filed Oct. 3, 2006, both incorporated by reference in their entireties.

BACKGROUND AND PRIOR ART

Despite improvements in the treatment of Non Small Cell Lung Cancer (NSCLC hereafter), current approaches for patients with more advanced disease such as chemotherapy and radiotherapy have had little impact on patient survival. See "Chemotherapy in non-small cell lung cancer: a meta-analysis using updated data on individual patients from 52 randomised clinical trials," *Non-small Cell Lung Cancer Collaborative Group Bmj*, 311:899-909 (1995); Socinski, et al., *Chest*, 123:226 S-243, (2003); Dubey and Schiller, *Hematol Oncol Clin North Am*, 18:101-114 (2004). An improvement in the understanding of molecular processes involved in pulmonary carcinogenesis has led to new treatment options with targeted small molecules and vaccines demonstrating encouraging potential. See Shepherd, et al., *N Engl J Med*, 353:123-132 (2005); Tsao, et al., *N Engl J Med*, 353:133-144 (2005); Zhang, et al., *Cancer Res*, 66: 9736-9743 (2006); O'Mahony, et al., *J Clin Oncol*, 23: 9022-9028 (2005); Hirschowitz, et al., *J Clin Oncol*, 22:2808-2815 (2004).

The heterogeneity of clinical outcome in lung cancer patients with similar stage disease, spontaneous regression of tumors and improved survival amongst patients with tumor-infiltrating lymphocytes and those who develop empyemas provide evidence that immune responses may influence outcome in NSCLC patients. See Shankaran, et al., *Nature*, 410: 1107-1111 (2001); Ruckdeschel, et al., *N Engl J Med*, 287: 1013-1017 (1972); Wei and Hang, *Immunol Invest*, 18:1095-1105 (1989). Utilizing the immune system to target lung carcinoma is thus an approach that should be further explored.

Cancer-testis antigens, or "CTAs", are members of a family of antigens expressed in cancer, with minimal expression in non-cancerous tissues. See, e.g., Tureci, et al., *Proc. Natl. Acad. Sci. USA*, 95:5211-5216 (1998); Gure, et al., *Int. J. Cancer*, 72:965-971 (1997); U.S. Pat. No. 6,140,050, all of which are incorporated by reference in their entireties. Many CTAs are immunogenic (Simpson, et al., *Nat Rev Cancer*, 5:615-625, (2005)), characterized by restricted expression in testis but aberrant expression in a variety of cancer types including NSCLC. See Scanlan, et al., *Cancer Immun*, 4:1 (2004). These properties render them attractive candidates for cancer vaccines. Indeed vaccination with either the full length recombinant CTA NY-ESO-1 protein, or CD4- or CD8-restricted peptide epitopes, enhances anti-NY-ESO-1 reactivity. See Maraskovsky, et al., *Clin Cancer Res*, 10: 2879-2890 (2004); Davis, et al., *Proc Natl Acad Sci USA*, 101: 10697-10702 (2004). Tumor regression has been achieved in some cases. See Jager, et al., *Proc Natl Acad Sci USA*, 97: 12198-12203 (2000).

Embryogenesis involves a de-programming or erasure of the epigenetic information governing differentiated cell behavior, thus returning the cell to the proliferative, undifferentiated, stem cell state. See Monk, et al., *Development*, 99: 371-382 (1987); Mayer, et al., *Nature*, 403: 501-502 (2000); Reik, et al., *Science*, 293: 1089-1093 (2001). By the blastocyst inner cell mass (ICM) and the PGC stages, the embryonic cells are totipotent stem cells (cells that can give rise to any and all adult cell types) capable of giving rise to immortal cell lines in vitro and teratomas in vivo. Embryonic genes which are active at this stage may be associated with similar properties of deprogramming, maintenance of the undifferentiated cell state, proliferation, invasiveness and indefinite growth of cancer cells. The identification of several Embryo-Cancer transcripts that are expressed in human pre-implantation embryos, absent in normal differentiated somatic tissues but re-expressed in tumor tissue, supports this hypothesis. See Monk, et al., *Oncogene*, 20:8085-8091 (2001), incorporated by reference in its entirety.

Monk, et al. described finding a portion of the gene referred to as Embryo-Cancer Sequence A (ECSA) in human pre-implantation embryos, primordial germ cells (PGCs) and several somatic tumors. This gene was subsequently renamed and entered into gene databases as Developmental Pluripotency Associated-2 (DPPA2). See Genbank Accession Number NM_138815, incorporated by reference and set forth at SEQ ID NO: 9. This gene maps to chromosome 3q13 over 8 exons and encodes a protein product of 297 amino acids. The primary protein structure contains a SAP motif and localizes to the nucleus.

Using a bioinformatics approach in the mouse, DPPA2, was found to have an expression pattern similar to OCT 3/4 (Bortvin, et al., *Development*, 130: 1673-1680 (2003)), one of several molecules including NANOG and SOX2 (Boiani, et al., *Nature Reviews Molecular Cell Biology*, 6: 872-881 (2005)), that are characteristically present in pluripotent stem cells (primordial cells that may still differentiate into various specialized types of tissue elements). The gene encoding DPPA4, another molecule which shares this expression pattern, lies 16 kB upstream of DPPA2 and encodes a closely related SAP domain. See Bortvin, et al., supra; Maldonado-Saldivia, et al., *Stem Cells*, 25: 19-28 (2007). These domains are thought to be involved in RNA metabolism and in the organization of nuclear architecture, suggesting that both may be involved in controlling cellular plasticity. See Aravind, et al., *Trends Biochem Sci*, 25: 112-114 (2000). DPPA2 and DPPA4 are both found exclusively in pluripotent cells; however a recent study involving murine embryonic stem cells suggests that DPPA4 may not be critical in maintenance of the pluripotent phenotype, as its over-expression did not inhibit cellular differentiation. See Ivanova, et al., *Nature*, 442: 533-538 (2006). Similarly, other markers including STELLAR, LEFTY2, and GDF3 are also expressed in pluripotent cells, although their roles are less well defined.

Germ cells also express a number of these molecules so it is not surprising that NANOG, OCT3/4, GDF3 and STELLAR have been found in germ cell tumors. See Chambers, et al., *Oncogene* 23: 7150-7160 (2004); Clark, et al., *Stem Cells* 22: 169-179 (2004); Hart, et al., *Cancer* 104: 2092-2098 (2005). In contrast, a few publications (limited to breast cancer (See Jin, et al., *Int J Cancer* 81: 104-112 (1999); Mongan, et al., *Mol Carcinog* (2006); Ponti, et al., *Cancer Res* 65: 5506-5511 (2005); Ezeh, et al., *Cancer* 104: 2255-2265 (2005) and bladder cancer (See Atlasi, et al., *Int J of Cancer*; 120: 1598-1602 (2007)) implicate these molecules in tumors arising from somatic cells. Their expression in somatic tumors may underpin biological functions that cancers share with embryonic cells, primordial germ cells and possibly adult stem cells, such as self renewal and proliferative potential. Suppression of differentiation is a hallmark of pluripotent embryonic cells, and although cancer cells may not necessarily have the capacity to proliferate along multiple differentiated lineages, loss of differentiation is a common feature.

Immunogenicity of these molecules in cancer patients has previously only been investigated for SOX2. Serum antibodies have been reported against SOX2 in meningioma and small cell lung cancer (SCLC) (Comtesse, et al., *PNAS* 102: 9601-9606 (2005); Gure, et al., *PNAS;* 97: 4198-4203 (2000)), although it is unclear how these responses arose since SOX2 expression was not documented in the meningiomas and expression in the SCLC patients was not investigated. A recent publication has also demonstrated SOX2 antibodies in patients with monoclonal gammopathy of undetermined significance (MGUS) in which the SOX2 defined the clonogenic cells. See Spisek, et al., *J. Exp. Med.* 2007 jem.20062387. In this study, the presence of serum antibody was also associated with T-cell responses and improved clinical outcome, although the numbers reported were small.

The experiments described herein explore the relationship between the embryo-associated antigen ECSA/DPPA2 and the germ-cell associated CT antigens (CTAs). The CTAs are not known to be markers of pluripotent stem cells although their expression in germ cells and various cancers, suggests a role in primitive cell populations. A recent review of the CTAs by Simpson et al provides a conceptual framework which links cancer with germ cell development. See Simpson, et al., *Nat Rev Cancer;* 5: 615-625 (2005). The authors suggest that the epigenetic dysregulation and subsequent de-repression of germ cell programs that would normally be silenced in somatic cells may contribute to de-differentiation and the subsequent malignant phenotype in cancer cells.

ECSA/DPPA2 can best be classified as an "Embryo-Cancer Antigen", as reflected by its association with embryogenesis rather than gametogenesis. Supporting this view is that ECSA/DPPA2 is expressed in pluripotent embryonic cells, human embryonic stem cell (hESC) lines as well as PGCs. In contrast, CTAs have not been reported to be expressed in hESCs or pre-implantation embryos. Secondly, ECSA/DPPA2 is co-expressed with other well defined markers of pluripotent stem cells including OCT3/4 and NANOG. See Monk, et al., supra; Maldonado-Saldivia, et al., supra. The association between these molecules and ECSA/DPPA2 is closely linked whereas a similar relationship with the CTAs has not been shown. Thus, ECSA/DPPA2 has unique associations since it belongs to a group of molecules that is implicated in pluripotent stem cells, on the one hand, and shares expression patterns in common with CTAs on the other.

SUMMARY OF THE INVENTION

It has now been found that the full length ECSA/DPPA2 gene, and its encoded protein, are found in additional types of cancer, as shown by the examples herein. Further, the following examples show specific expression of ECSA/DPPA2 in a subpopulation of putative stem cells in NSCLC and demonstrate its ability to invoke spontaneous immune responses in vivo, suggesting a therapeutic use for both the protein and nucleic acid molecules encoding it, i.e., as a therapeutic and/or preventive vaccine, for example. Hence, a further feature of the invention is a method for preventing or treating cancer via administering to a patient with cancer, an amount of ECSA/DPPA2 or a nucleic acid encoding it, sufficient to prevent or to alleviate said cancer. The therapeutic agent may be administered, e.g., in any of the standard therapeutic forms for protein or DNA based therapies, in a therapeutically effective amount.

This amount will vary, based upon the patient, who is preferably a human being. Preferably, the patient is one suffering from non-small cell lung carcinoma, mesothelioma, melanoma, or lymphoma.

The following examples further show that ECSA/DPPA2 is also co-expressed with many CTAs.

It is therefore an object of the present invention to determine presence of a cancer by assaying a tumor sample for expression of full length ECSA/DPPA-2 and/or presence of its encoded protein. ECSA/DPPA2 can also be used as a therapeutic target or agent for antigen specific immunotherapy in cancer.

DETAILED DESCRIPTION

Example 1

The following experiments were conducted to determine expression of ECSA/DPPA2 in normal and malignant tissues.

A series of intron spanning primers for the ECSA/DPPA2 expression sequence were designed for use in RT-PCR, as were custom designed probes for use in quantitative RT-PCR.

These primers were then used in assays on frozen and paraffin embedded tumor samples, testis and embryonic stem cells, and a variety of normal tissues including brain, placenta, liver, heart, kidney, lung, bone marrow, colon, small intestine, spleen, stomach and thymus, using standard techniques.

A total of 110 tumor specimens were obtained from patients with non-small cell lung cancer (NSCLC), as were sera samples from 104 of these patients. These samples were used for screening and serological investigations. Additionally, a total of 200 tumor samples representing a panel of malignancies (hepatocellular, NSCLC, melanoma, colon carcinoma, non-Hodgkins lymphoma, mesothelioma, Hodgkins lymphoma, rectal carcinoma, renal cell carcinoma, transitional cell carcinoma, cholangiocarcinoma, follicular carcinoma, breast carcinoma) at various clinical stages which had been snap frozen in liquid nitrogen and stored at −80° C. were utilized for the extraction of total RNA. Total RNA from normal tissues including brain, placenta, liver, heart, kidney, lung, bone marrow, colon, small intestine, spleen, stomach and thymus were obtained from commercial sources.

Briefly, total RNA was isolated in accordance with standard methods. First strand cDNA was synthesized from 2 µg of total RNA in a 20 µL reaction using 1 µg of random hexamer primer, 1 mmol/L deoxynucleoside triphosphate, 40 units of RNase inhibitor and 10 units Moloney Murine Leukemia Virus reverse transcriptase for 60 minutes at 42° C. Reverse transcriptase was omitted for negative controls.

One µl of cDNA (100 ng of total RNA) was used in each PCR reaction with a final concentration of 2 mmol/l magnesium chloride, 0.02 mmol/l deoxynucleoside triphosphate, 0.625 units of DNA polymerase and 2 ng of primers. Two different sets of PCR primers were used: ECSA Fwd, 5'-AGACCAGATTACAGCGATGT (SEQ ID NO: 1) and ECSA Rev 5'-CGTAATAGGTTACATGATCTG (SEQ ID NO: 2) which amplified a gene fragment of 546 base pairs; and DPPA Fwd, 5'-GCCCTTTGTTTATGGCCTGA (SEQ ID NO: 3) and DPPA Rev, 5'-ACGCTTGGTTC-CATTTGTTC (SEQ ID NO: 4) which amplified a gene fragment of 430 base pairs. PCR was performed using 35 amplification cycles at an annealing temperature of 50° C. or 60° C. respectively. Other primers for CTAs were also used. PCR products were then visualized on a 1% agarose/ethidium bromide gel.

For quantitative real time PCR, intron-spanning multiplex assays were designed using the Universal Probe Library (UPL) assay design. All reactions were carried out in duplicate using the ABI 7700 Prism Sequence Detector. Primers used were ECSA-L, 5'-ACCCTGAACAACGGCAAG (SEQ ID NO: 5) and ECSA-R, 5'-TTGCGTTTCCTCGAACATC (SEQ ID NO: 6) along with commercially available primers. In brief, 1 µl of cDNA was added to 24 µl of reaction mixture containing 12.5 µl commercially available PCR reagents, 1.25 µl probe (final concentration 100 nM) 1.25 µl 18 S pre-developed assay reagents (PDAR) and 2.5 µl primers (final concentration 300 nM). Thermal cycler conditions were as follows: 50° C. for 2 minutes, 95° C. for 10 minutes followed by 40 cycles of 94° C. for 20 seconds and 60° C. for 45 seconds. All results were normalized to 18 S amplification. Relative expression was calculated using the target threshold ($C_T$) value for testis or normal lung as a calibrator in accordance with Livak and Schmittgen, Methods, 25: 402-408 (2001).

With respect to normal tissue, ECSA/DPPA2 transcripts were primarily found in testis, although low level expression was also found in placenta, bone marrow, thymus and kidney. Immunohistochemistry (IHC) of normal kidney sections did not show staining. The transcript was present in 8 of 27 (30%) NSCLC from the 200 sample set and 33 of 110 (30%) of the NSCLC tumors from the other sample set, as well as in melanomas, colorectal cancers and lymphomas. The ECSA/DPPA2 gene transcript was present in squamous cell, adenocarcinoma and large cell tumors. Squamous cell carcinomas expressed the gene at higher levels compared to other histological subtypes. The degree of differentiation was also not correlated with ECSA/DPPA2 expression.

Example 2

Immunohistochemistry (IHC) was then conducted to determine the location of DPPA2 protein in cells.

For detection of ECSA/DPPA2 protein, five micron sections from stored frozen tissues were cut and were fixed by immersion in cool acetone for 30 minutes. For paraffin sections, four micron formalin-fixed sections were prepared and dried overnight at 37° C. These were de-waxed in xylene and rehydrated using alcohols. Water bath retrieval was performed for 20 minutes using EDTA buffer pH 8.0. Endogenous peroxidase activity was quenched with 0.3% hydrogen peroxide for 10 minutes. Following 10 minutes of blocking with commercially available protein blocking agents, sections were incubated with affinity purified ECSA/DPPA2 specific rabbit polyclonal antibody diluted in PBS at 1 to 400 for a period of 1 hour, at room temperature. Negative controls omitting the primary antibody and with a rabbit polyclonal antibody control were also incubated in parallel. Commercially available horseradish peroxidase (HRP) labeled polymer was added and incubated at room temperature for 30 minutes. Immunodetection was carried out by incubating the slides in 3-amino-9-ethyl-carbazole and counterstaining with haematoxylin before completing the assay.

Commercially available anti-NY-ESO-1 (E978) and MAGE-C1 (CT7-33), antibodies were used at a concentration of 2.5 µg/mL for E978, and a 1:40,000 dilution for CT7-33. Antigen retrieval was performed for 20 minutes using EDTA buffer pH 8.0 for E978 and citrate buffer pH 6.0 for CT7-33. HRP-labeled polymer was used as the secondary and immunodetection performed as described above. A mouse IgG1 isotype control was incubated in parallel.

For double staining, sections were treated as described. ECSA/DPPA2 specific rabbit polyclonal antibody was diluted 1:800 and stained using Envision+™ HRP-labeled polymer as the secondary antibody and 3,3' Diaminobenzidine (DAB) as the chromagen. NY-ESO-1 (E978) was used at the concentration described previously, and stained using the commercially available alkaline phosphatase (AP) labeled polymer and visualized using fuchsin as the chromogen.

The results confirmed nuclear staining of spermatogonia, human embryonic stem cells (hESCs) and isolated cells in lung cancer, but not in any of the other normal tissues screened. Normal lung was carefully examined in order to identify staining of potential pulmonary stem cells. These experiments failed to demonstrate ECSA/DPPA2 in alveoli, the bronchioalveolar junction, the terminal bronchioles, the primary bronchioles and larger airways.

Example 3

Since CTAs are commonly expressed in NSCLC, the following experiments were conducted to determine if ECSA/DPPA2 expression was correlated with CTA expression.

Primers for a panel of CTAs were used to investigate gene transcripts in resected NSCLC using conventional PCR. Tumors were grouped according to expression of ECSA/DPPA2 and then analyzed using a $\chi^2$ test to determine if the frequencies of CTA expression were significantly different between ECSA/DPPA2 positive and ECSA/DPPA2 negative samples.

The results showed that the ECSA/DPPA2 positive tumors expressed CTAs located on the X-Chromosome (CT-X) antigens such as the MAGE family, LAGE and NY-ESO-1 at a much higher rate than the ECSA/DPPA2 negative tumors ($\chi^2$ test, p<0.001). MAGE-A4, in particular, was expressed in 85% of ECSA/DPPA2 positive tumors compared with only 15% of ECSA/DPPA2 negative tumors. BORIS, a CTA not located on the X-chromosome (Non-X CT), was also more likely to be expressed in ECSA/DPPA2 positive tumors.

IHC was also carried out as described supra. The results showed co-expression of NY-ESO-1 and ECSA/DPPA2, but not co-expression of MAGE-C1 protein in a NSCLC. Notably, a defined subpopulation of lung carcinoma cells stained positively for ECSA/DPPA2 protein. In contrast, NY-ESO-1 and MAGE-C1 stained many more cells within the tumor, although still within defined areas. The subpopulation of cells which stained positively for ECSA/DPPA2 were large basally located cells adjacent to stroma; an area reported to be a niche for cancer stem cells. See Prince, et al., *Proc Natl Acad Sci USA* (2007). Smaller and more centrally located cells stained negatively for ECSA/DPPA2 within the same tumor sample. The low abundance of positively staining putative cancer stein cells parallels the quantitative PCR results showing low levels of ECSA/DPPA2 transcript in the NSCLCs surveyed.

Example 4

Due to the co-expression of ECSA/DPPA2 transcripts with CTAs, the following experiments were conducted to investigate whether ECSA/DPPA2 was spontaneously immunogenic in NSCLC patients by determining presence of IgG antibodies in sera.

First, recombinant ECSA/DPPA2 was generated. For prokaryotic expression construction of ECSA/DPPA2, a commercially available vector containing cDNA encoding ECSA/DPPA2 was amplified via PCR with the following primers: 5'-TTTT GGATCC ATG TCA GAT GCA AAT TTG GAT (SEQ ID NO: 7) and 3'-TTTT CTCGAG CTA CTT CTC TAC TGT CAT TAA (SEQ ID NO: 8) (underlining indicates the restriction sites), corresponding to an amplification product of nucleotides 126-1022. Polymerase chain reaction-amplified products were inserted into the E. coli expression vector PGEX-4T, between BamH1 and XhoI restriction sites. The resulting fusion protein (amino acids 1-298) was translated in-frame from the vector's start codon. After sequence verification, the prokaryotic expression vector pGEX-4T-DPPA2 was introduced into E. coli following standard protocols and the expression of fusion protein was induced by adding isopropyl-β-D-thiopgalactopyranoside (IPTG). The fusion protein was purified using a standard GST tag. After 10% SDS-PAGE analysis, a band of 60 kDa was found from the sample of fusion proteins purified by glutathione-sepharose beads.

Next, ECSA/DPPA2 antibodies were produced. New Zealand rabbits were injected subcutaneously with 50 μg of the recombinant ECSA/DPPA2 antigen described above. For the first immunization, the antigen was admixed 1:1 with complete Freund's adjuvant; for the next four boosts (on days 28, 42, 60 and 78) incomplete Freund's adjuvant was used.

Anti-ECSA/DPPA2 antibody production was determined by testing in an enzyme-linked immunosorbent assay (ELISA) in accordance with standard methods.

Affinity purification was achieved by coupling 1 mg of fusion protein to activated Sepharose 4B beads in accordance with the manufacturer's instruction. After conjugation the beads were washed three times with PBS and 25 mL of rabbit antiserum was added to the beads. The 5 mL column was washed once with 1M Tris-HCl pH 8.0 and once with 1M Tris pH HCl, pH 5.0. The specific antibody was then eluted in 1 M Tris pH 2.5).

Detection of specific serum antibody to ECSA/DPPA2 and NY-ESO-1 were performed by indirect ELISA. Briefly, commercially available ELISA plates were coated with 1.5 μg/mL of recombinant ECSA/DPPA2 or 3 μg/mL NY-ESO-1 protein (50 μL/well) and incubated overnight at 4° C. After washing with 0.2% Tween20 and blocking with 0.1% human serum albumin (blocking buffer), serum samples diluted in blocking buffer at a 1 to 400 dilution, were incubated at room temperature for one hour. As the recombinant proteins were produced in E. coli, all sera were pre-adsorbed with E. coli lysates for 1 hour at 4° C. to remove potential contamination of serum E. coli antibodies which are often found in normal sera.

After further washing, alkaline phosphatase-conjugated affinity purified sheep anti-human IgG diluted in blocking buffer at 1:1000 dilution was added for one hour at room temperature.

Next, P-nitrophenyl phosphate substrate, carbonate buffer and 2% magnesium chloride were added for 30 minutes at room temperature, after which development was stopped using 3M sodium hydroxide. Excitation at 450/50 and emission at 580/50 with a gain of 25 was read using an ELISA plate reader.

The results showed that high affinity IgG antibodies were detected in 4% (4 of 104) of patients with NSCLC but none of the 18 normal sera screened. All of the sera tested were from resected early stage NSCLC, thereby limiting the potential exposure of tumor antigens to the immune system.

Western blots were then performed in accordance with standard methods to confirm the positive ELISA results for ECSA/DPPA2. Briefly, purified denatured recombinant ECSA/DPPA2 proteins were separated using 4-12% SDS-PAGE and transferred to PVDF membranes. E. coli pre-adsorbed sera (as described supra) in 1% skim milk and 0.05% Tween at a final dilution of 1 in 1000 were incubated for one hour at room temperature with the membranes and then washed in PBS. HRP conjugated goat anti-human antibody was added to the membrane at a 1 in 10,000 dilution for 30 minutes. Chemifluorescent detection was performed using standard ECL methodologies.

Of the four seropositive patients, two showed high expression of ECSA/DPPA2 antigen in their tumors, while two did not express the antigen. It is unclear whether the two patients who were ECSA/DPPA2 antibody positive but whose tumors were absent for the antigen represent background signal, or whether their antibody responses affected tumor antigen expression.

NY-ESO-1 protein (produced in E. coli) was used as a specificity control to determine if responses to the ECSA/DPPA2 protein were against contaminating bacterial protein. Thirteen patients including those known to be seropositive for ECSA/DPPA2 antibody and NY-ESO-1 antigen were screened for NY-ESO-1 antibodies. The ECSA/DPPA2 positive sera were negative for NY-ESO-1. Two serum samples contained high affinity antibodies to NY-ESO-1, but there was no overlap with ECSA/DPPA2 positive samples, indicating that these were true NY-ESO-1-specific antibody responses.

The foregoing examples demonstrate that ECSA/DPPA2, is a human cancer antigen that is predominantly expressed in NSCLC but also in other malignancies including, but not limited to, colorectal cancer, lymphoma and melanoma. It is expressed in a subpopulation of putative stem cells, suggesting a role as a cancer stem cell marker appears to induce spontaneous immune responses in lung cancer patients and demonstrates an unique association with the majority of the tested Cancer-Testis Antigens.

Hence, ECSA/DPPA2 can be used diagnostically as a target by the skilled artisan, for determination of cancer such as in a subject. The determination of expression can be carried out via, e.g., determination of transcripts of the gene via any of the standard nucleic acid hybridization assays, such as polymerase chain reaction. In a preferred embodiment, one determines presence of a transcript of the gene by contacting a sample with a nucleic acid molecule which specifically hybridizes to the transcript, such as the specific primers listed.

The spontaneous immune responses invoked in vivo, as discussed supra, also suggest a role for the molecule in therapy, either as a preventive or therapeutic vaccine. Administration of either the protein or a nucleic acid molecule are features of this aspect of the invention, as described supra.

Other features and applications of the invention will be clear to the skilled artisan, and need not be set forth herein.

We claim:

1. A method for determining presence of a cancer comprising assaying a tumor sample for expression of full length DPPA-2 consisting of the nucleotide sequence of SEQ ID NO: 9 or a protein expressed thereby, presence thereof being indicative of said cancer, wherein said sample is not from testis, placenta, bone marrow, thymus or kidney cells.

2. The method of claim 1, wherein said cancer is non-small cell lung carcinoma, mesothelioma, melanoma or lymphoma.

3. The method of claim 1, wherein said assay is a nucleic acid hybridization assay.

4. The method of claim 3, wherein said nucleic acid hybridization assay is a polymerase chain reaction.

5. The method of claim 1, wherein said method comprises an immunoassay.

* * * * *

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence

```
<220> FEATURE:
<223> OTHER INFORMATION: Synthetic Primer

<400> SEQUENCE: 1
agaccagatt acagcgatgt                                                    20

<210> SEQ ID NO 2
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2
cgtaataggt tacatgatct g                                                  21

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3 gcccttttgtt tatggcctga                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
acgcttggtt ccatttgttc                                                    20

<210> SEQ ID NO 5
<211> LENGTH: 18
<212> TYPE: DNA
<213> ORGANISM: Artificial Sequence
<220> FEATURE:
<223> OTHER INFORMATION: Synthetic Primer

<400> SEQUENCE: 5
accctgaaca acggcaag                                                      18

<210> SEQ ID NO 6
<211> LENGTH: 19
<212> TYPE: DNA
<213> ORGANISM: Artificial Sequence
<220> FEATURE:
<223> OTHER INFORMATION: Synthetic Primer

<400> SEQUENCE: 6
ttgcgtttcc tcgaacatc                                                     19

<210> SEQ ID NO 7
<211> LENGTH: 31
<212> TYPE: DNA
<213> ORGANISM: Artificial Sequence
<220> FEATURE:
<223> OTHER INFORMATION: Synthetic Primer

<400> SEQUENCE: 7
ttttggatcc atgtcagatg caaatttgga t                                       31
```

```
<210> SEQ ID NO 8
<211> LENGTH: 31
<212> TYPE: DNA
<213> ORGANISM: Artificial Sequence
<220> FEATURE:
<223> OTHER INFORMATION: Synthetic Primer

<400> SEQUENCE: 8
ttttctcgag ctacttctct actgtcatta a                                31

<210> SEQ ID NO 9
<211> LENGTH: 940
<212> TYPE: DNA
<213> ORGANISM: H. Sapiens

<400> SEQUENCE: 9
acttcaaaca aatgagcaat ttacagctcc acaaaaagct agatgcaaaa taccagccct    60
tcccttgccg accattttgc ctcccattaa taaggtgtgt cgggacactt tgcgggactg   120
gtgtcaacaa ctcggtttga gtactaatgg caagaaaatc gaagtttatc tgaggcttca   180
taggcatgct taccctgaac aacggcaaga tatgcctgaa atgtcacaag agaccagatt   240
acagcgatgt tcgaggaaac gcaaggcagt gaccaagaga gcaaggcttc agagaagtta   300
tgagatgaat gagagagcag aagagaccaa tacagttgaa gtgataactt cagcaccggg   360
agccatgttg gcatcatggg caagaattgc tgcaagagct gttcagccta aggctttgaa   420
ttcatgttcc attcctgttt ctgttgaggc ctttttgatg caagcctctg tgtcaggtg    480 gtgtgtggtc catggcagac ttctctcggc agacacaaag ggttgggtac gcctgcagtt   540
tcatgcaggt caggcctggg tgcctaccac tcacaggagg atgatttctc tcttcttgtt   600
acctgcctgc attttcccat ccccaggcat agaagataat atgttatgcc ccgactgtgc   660
taagaggaat aagaagatga tgaaaagatt aatgacagta gagaagtagc agcaacctgt   720
ttgaatacaa tgtactaaag gagggatgta ctttcagatc atgtaaccta ttacgaagga   780
gtggaagagg agacaatttg aatgaatcct catgatctac aaaacaaaat catagtgact   840
aggactccac agtgaagatg gttgactagt gacacagccc catctaaaga atcccttctc   900
gtatgtctga aaacccatta aaataaagtc actgcaaaaa                         940
```